United States Patent
Bassaganya-Riera et al.

(10) Patent No.: US 11,026,888 B1
(45) Date of Patent: Jun. 8, 2021

(54) FUNCTIONAL BEVERAGE COMPOSITIONS AND METHODS OF USING AND MAKING SAME

(71) Applicant: Nutrition Therapeutics, Inc., Blacksburg, VA (US)

(72) Inventors: Josep Bassaganya-Riera, Blacksburg, VA (US); Nathan Briggs, Blacksburg, VA (US); Raquel Hontecillas-Magarzo, Blacksburg, VA (US)

(73) Assignee: NUTRITION THERAPEUTICS, INC., Blacksburg, VA (US)

( * ) Notice: Subject to any disclaimer, the term of this patent is extended or adjusted under 35 U.S.C. 154(b) by 0 days.

(21) Appl. No.: 16/735,391

(22) Filed: Jan. 6, 2020

Related U.S. Application Data

(60) Provisional application No. 62/788,397, filed on Jan. 4, 2019.

(51) Int. Cl.
| | |
|---|---|
| *A61K 36/00* | (2006.01) |
| *A61K 9/00* | (2006.01) |
| *A61K 31/202* | (2006.01) |
| *A61K 9/107* | (2006.01) |
| *A61K 36/185* | (2006.01) |
| *A61P 29/00* | (2006.01) |
| *A61K 47/24* | (2006.01) |

(52) U.S. Cl.
CPC ............ *A61K 9/0095* (2013.01); *A61K 9/107* (2013.01); *A61K 31/202* (2013.01); *A61K 36/185* (2013.01); *A61K 47/24* (2013.01); *A61P 29/00* (2018.01)

(58) Field of Classification Search
CPC .................................................. A61K 36/00
USPC ........................................................ 424/725
See application file for complete search history.

(56) References Cited

U.S. PATENT DOCUMENTS

| | | |
|---|---|---|
| 6,410,588 B1 | 6/2002 | Feldmann et al. |
| 6,630,163 B1 | 10/2003 | Murad |
| 6,630,507 B1 | 10/2003 | Hampson et al. |
| 8,258,188 B2 | 9/2012 | Bassaganya-Riera |
| 8,822,543 B2 | 9/2014 | Bassaganya-Riera |
| 2010/0286098 A1 | 11/2010 | Robson et al. |
| 2012/0251685 A1 | 10/2012 | Wang-Nolan et al. |
| 2017/0020945 A1 | 1/2017 | Reillo et al. |
| 2017/0150743 A1 | 6/2017 | Yang et al. |
| 2017/0188605 A1 | 7/2017 | Franklin et al. |
| 2018/0125980 A1 | 5/2018 | Finley et al. |

FOREIGN PATENT DOCUMENTS

| | | |
|---|---|---|
| WO | WO 2012/144892 A1 | 10/2012 |
| WO | WO 2015086268 A1 * | 6/2015 |
| WO | WO 2017/045053 A1 | 3/2017 |
| WO | WO 2018/006165 A1 | 1/2018 |
| WO | WO 2018/061007 A1 | 4/2018 |
| WO | WO 2018/102029 A1 | 6/2018 |

OTHER PUBLICATIONS

Banihani, S. et al. "Pomegranate and type 2 diabetes." *Nutrition Research* 33 (2013): 341-348.

Couch DG, et al. "Cannabidiol and palmitoylethanolamide are anti-inflammatory in the acutely inflamed human colon." *Clin Sci (Lond).* 2017; 131(21):2611-2626.

De Filippis D, et al. "Cannabidiol reduces intestinal inflammation through the control of neuroimmune axis." *PLoS One.* 2011;6(12):e28159).

Jadoon, K., et al. *Diabetes Care* 2016; 39: 1-10.

Kim, et al. "Comparison of anti-inflammatory mechanisms of mango (*Mangifera indica* L.) and pomegranate (*Punica granatum* L.) in a preclinical model of colitis." *Mol Nutr Food Res.* Sep. 2016; 60(9): 1912-1923.

McCallum and Bashashati, "Cannabis in Gastrointestinal Disorders." *Practical Gastroenterology.* Dec. 2014; 4: 36-46.

* cited by examiner

*Primary Examiner* — Michael V Meller
(74) *Attorney, Agent, or Firm* — Daniel A. Blasiole; DeWitt LLP

(57) ABSTRACT

Functional beverage compositions in liquid form. The functional beverage compositions include water, lecithin, a punicic acid-containing oil, and a cannabinoid-containing oil. The punicic acid-containing oil and the cannabinoid-containing oil are stably suspended within the water. Methods of using the compositions include administering the compositions to reduce inflammation in a subject or treat an inflammation-related disease in a subject. Methods of making the compositions include suspending the punicic acid-containing oil and the cannabinoid-containing oil in a sub-volume of water and adding additional water to arrive at a final composition volume.

14 Claims, 11 Drawing Sheets

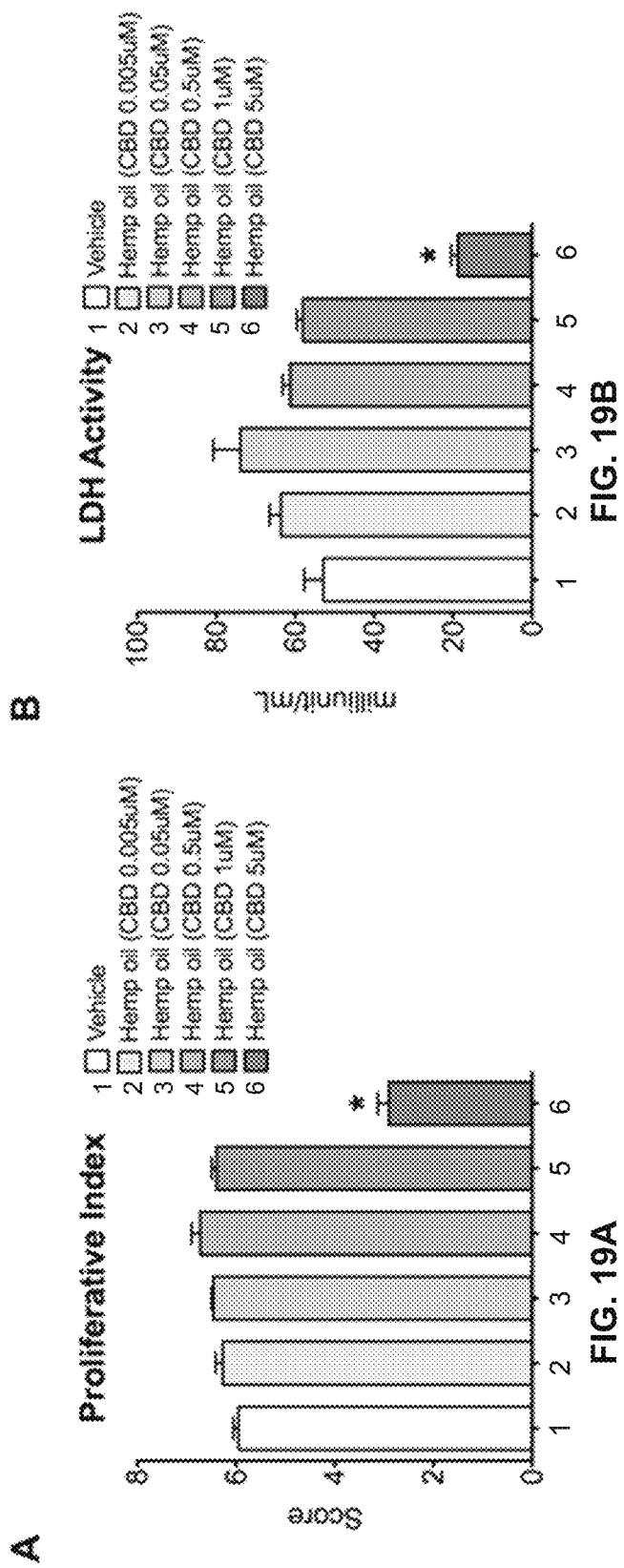

US 11,026,888 B1

FUNCTIONAL BEVERAGE COMPOSITIONS AND METHODS OF USING AND MAKING SAME

FIELD OF THE INVENTION

The present invention is generally directed to functional beverage compositions comprising biologically active compounds, methods of using the compositions, and methods of making the compositions.

BACKGROUND

Consumers are continually seeking functional food and beverage products to maintain, promote, or improve upon a healthy lifestyle and health condition. For example, consumers incorporate foods and beverages containing increased levels and/or combinations of biologically active compounds in their diet to promote or increase the health of their physical or emotional state. More frequently, consumers seek functional food and beverage products made from one or more all-natural ingredients to manage, mitigate, or otherwise control symptoms of minor or major disease states (e.g., Crohn's Disease, diabetes, hypertension, etc.), provide relief to chronic or acute afflictions (e.g., abdominal pain, constipation, etc.), attenuate transitory conditions (e.g., headaches, exhaustion, anxiety, intestinal bloating, sleeplessness, etc.), or prevent unhealthy conditions and maintain a healthy state. A functional beverage can be effective against or provide healthful maintenance from a multitude of disease states or unhealthy conditions in a single, convenient product form. Consumers would find beneficial a multifunctional beverage composition provided in effective concentrations over recommended serving sizes and effective towards multiple health applications.

An individual's state of health can be interdependent on more than one input; for example, stress, anxiety and the loss of sleep can affect immune response effectiveness, and the compromised immune response can then impact intestinal health or responses to, for example, systemic infections. Therefore, there is a need for a novel preventive and/or therapeutic multifunctional beverage composition that can be effective for treating multiple disease states and conditions or maintenance of one or more health aspects of individuals.

Historically, consumers have sought biologically active compounds in the form of nutraceuticals such as vitamin and mineral supplements, either in "pill" form or as fortifying components or additives to foods and beverages. However, the use and easy availability of these common nutraceuticals often overshadows the efficacy and bioavailability of both traditional and less widely known nutraceuticals in their natural form or other less common natural biologically active compounds found in other indigenous food sources. Research findings underscore the effectiveness of natural forms of biologically active compounds wherein absorption rates into the body are enhanced or, when combined with other biologically active compounds, provide a synergistic benefit to the consumer. Novel natural medicines and biologically active compounds in natural form (or extracted from natural sources) are thus sought after as alternatives to conventional treatments and for the maintenance of good health. Therefore, there is an ongoing need for the formulations of natural biologically active compounds and natural sources for biologically active compounds as more effective active ingredients of functional beverages. There is also a need for determining combinations or applications of natural biologically active compound products and applying them to functional foods and beverages formulated as a daily dietary supplement, preventative treatment or for clinical applications treating systemic or chronic disease states and disorders.

SUMMARY OF THE INVENTION

The present invention is generally directed to functional beverage compositions and methods of using and making same.

The present invention provides functional beverage compositions that contain punicic acid and cannabinoids. The compositions can be provided in a liquid form that stably maintains the punicic acid and cannabinoids in stable oil-in-water suspensions. The compositions can be effective for multiple health related conditions as well as the promotion of gastrointestinal health and well-being. The punicic acid and cannabinoids in the compositions provided herein have synergistic activities targeted for a number of desired outcomes, for example, health maintenance, disease prevention, and or disease treatment, including but not limited to diseases or conditions relating to inflammation. The functional beverage compositions optionally also include additional nutraceutical and/or functional ingredients effective for one or more health benefits. The functional beverage compositions described herein provide a convenient and improved way for individuals to consume a beverage containing biologically active compounds in a form and concentration to promote significant improvement in inflammation reduction, gastrointestinal health, neurological/mental health, blood glucose levels, and general well-being. These compositions can be used for the treatment and or maintenance of gut health, mental/emotional health, immunity, and control of blood sugar levels.

Accordingly, methods for health maintenance or treatment of diseases with the compositions of the invention herein are also provided. The compositions, for example, can be used decreasing inflammation in a subject by administering the compositions orally to a subject.

Methods of making the compositions of the invention are also provided.

The objects and advantages of the invention will appear more fully from the following detailed description of the preferred embodiment of the invention made in conjunction with the accompanying drawings.

BRIEF DESCRIPTION OF THE DRAWINGS

FIG. 1 shows the pomegranate seed oil as a layer on the surface of the water. FIG. 2 shows the clarity of the mixture.

FIG. 3 shows CBD as a buoyant, non-dissolving solid floating on top of the water. FIG. 4 shows the clarity of the mixture.

FIG. 5 shows that CBD is soluble in the pomegranate seed oil but that the CBD and pomegranate seed oil are immiscible in the water. FIG. 6 shows the clarity of the mixture.

FIG. 7 shows a very small oil layer with no visible solids on top of the water. FIG. 8 shows the clarity of the mixture.

FIG. 9 shows no oil layer or visible solids on top of the water. FIG. 10 shows the clarity of the mixture.

In FIG. 11, the components were added one at a time. In FIG. 12, the pomegranate seed oil and the full spectrum hemp oil were pre-mixed before adding to the water. Both cases resulted in a hazy beverage with oil droplets visible on the surface.

In FIG. 14, the lecithin was not hydrated with the water before mixing with the other components, which resulted in a very hazy drink, with small but noticeable oil droplets visible on the surface. In FIG. 15, the lecithin was hydrated with the water before mixing with the other components, which resulted in a very hazy drink with negligible visible oil phase.

FIGS. 19A-B show the effect of full spectrum hemp oil on the proliferation (FIG. 19A) and glucose metabolism (FIG. 19B) of CD4+ T cells. *p<0.05.

DETAILED DESCRIPTION OF THE INVENTION

Figure 1:
FIGS. 1 and 2 show results of vigorously mixing water and pomegranate seed oil.

Provided herein are functional beverage compositions. Functional beverage compositions are liquid compositions supplemented or fortified with biologically active compounds. The biologically active compounds are preferably included in the functional beverage compositions in amounts that provide enhancing benefits (health, nutritional, etc.) to the consumer. The enhancing benefit can be quantitative, qualitative or subjective, and promote or maintain health or contribute to disease prevention.

Punicic acid is a biologically active compound that can be included in the compositions of the invention. Punicic acid is naturally found in seeds of pomegranate, i.e., *Punica granatum*, representing over 60 percent of the seed oil. Punicic acid is a conjugated α-linolenic acid (CLnA). Punicic acid contains three double bonds (cis-9, trans-11, and cis-13), and is known as an 18:3 fatty acid. It is an omega-5 long chain polyunsaturated fatty acid and a positional and geometric isomer of α-linolenic acid. Punicic acid is also present in other plants such as *Momordica balsamina*.

The punicic acid in the compositions of the invention can be included in the form of pomegranate seed oil. Pomegranate seed oil is a non-toxic, natural, orally active food ingredient. Approximately 12-20% of total pomegranate seed weight is comprised of pomegranate seed oil. Conjugated octadecatrienoic fatty acids make up approximately 80% by weight of seed contents and pomegranate seed oil is considered to be a rich source of those fatty acids; in particular, punicic acid (cis-9, trans-11, cis-13 acid) being the primary fatty acid among them. Other isomers of conjugated linolenic acids (CLnAs) are catalpic acid (C18:3-9-trans,11-trans,13-cis) and α-eleostearic acid (C18:3-9-cis, 11-trans, 13-trans). Total lipids in pomegranate seed oil are comprised mainly of various triglycerides.

Cannabinoids are other biologically active compounds that can be included in the compositions of the invention. Cannabinoids (which include phytocannabinoids) are a group of psychoactive and non-psychoactive that can be extracted and/or isolated from the *Cannabis* plants or cultivars or can be synthetically manufactured. Cannabinoids include one or more of the chemical compounds cannabigerolic acid; cannabigerolic acid monomethylether; cannabigerol; cannabigerol monomethylether; cannabigerovarinic acid; cannabigerovarin; cannabichromenic acid; cannabichromene; cannabichromevarinic acid; cannabichromevarin; cannabidiolic acid; cannabidiol; cannabidiol monomethylether; cannabidiol-C4; cannabidivarinic acid; cannabidiorcol; delta-9-tetrahydrocannabinolic acid A; delta-9-tetrahydrocannabinolic acid B; delta-9 tetrahydrocannabinol; delta-9-tetrahydrocannabinolic acid-C4; delta-9-tetrahydrocannabinol-C4;delta-9-tetrahydrocannabivarinic acid; delta-9-tetrahydrocannabivarin; delta-9-tetrahydrocannabiorcolic acid; delta-9-tetrahydrocannabiorcol; delta-7-cis-iso-tetrahydrocannabivarin, delta-8-tetrahydrocannabinolic acid A; delta-8-tetrahydrocannabinol-A; cannabicyclolic acid; cannabicyclol; cannabicyclovarin; cannabielsoic acid A; cannabielsoic acid B; cannabielsoin; cannabinolic acid; cannabinol; cannabinol methylether; cannabinol-C4; cannabivarin; cannabinol-O; cannabiorcol; cannabinodiol; cannabinodivarin; cannabitriol; 10-ethoxy-9-hydroxy-delta-6a-tetrahydrocannabinol; 8,9-dihydroxy-delta-6a-tetrahydrocannabinol; cannabitriolvarin; ethoxy-cannabitriolvarin; dehydrocannabifuran; cannabifuran; cannabichromanon; cannabicitran; 10-oxo-delta-6a-tetrahydrocannabinol; delta-9-ci s-tetrahydrocannabinol; 3,4,5,6-tetrahtdro-7-hydroxy-a-a-2-trimethyl-9-n-propyl-2,6-methano-2H-lbenzoxocin-5-methanol; cannabiripsol; trihydroxy-delta-9-tetrahydroxycannabinol. As used herein, the term "cannabinoid" can refer to any one or more, in any combination, of the cannabinoid chemical compounds described. The term "phytocannabinoid" can refer to cannabinoid compounds extracted from a natural resource, such as the *Cannabis* plant and cultivars related thereto. In some embodiments, the cannabinoid can be provided in the compositions of the invention in the form of full spectrum hemp oil.

Generally, cannabinoids are similar to the neurotransmitter endocannabioids the body makes which have neurotransmitter activity on cannabinoid receptors in cells involved with appetite, memory, movement, and pain. While some components (specifically, delta-9 tetrahydrocannabinol) are psychoactive compounds with long-lasting effects on the user, many of the of the other cannabinoids are not identified as a psychotropic agent and are considered safe for consumption in various routes of administration. Both categories of compounds are typically found as a mixture, at various concentration ranges, in the plant source. For formulating into pharmaceutical compositions, the cannabinoids are often extracted from the plant source by various methods, or synthetically manufactured. Cannabinoid formulations can contain effective concentrations of psychotropic cannabinoids for eliciting a psychotropic response, or can be comprised of minor concentrations of psychotropic cannabinoids, for example cannabinoid compositions derived from hemp (e.g., hemp oil, etc.).

The combination of punicic acid with the cannabinoids in the compositions of the invention provide synergistic effects and provide benefits against various health ailments. The presence of punicic acid and cannabinoids in the compositions of the invention can provide cytotoxic and antitumor properties, body fat-reducing effects, and lipid metabolism-normalizing effects, in vivo immune system enhancement, preventive activity against hormone-related (prostate and breast) and colon cancers, reduction of the accumulation of hepatic triglycerides, and promotion of epidermal tissue regeneration. Antioxidant and anti-inflammatory activities of the combination of the punicic acid and cannabinoids can result from inhibition of lipid peroxidation and neutrophil activation. The combination of the punicic acid and cannabinoids can reduce body weight, reduce leptin levels, reduce insulin levels, enhance glucose tolerance, improve peripheral insulin sensitivity, increase carbohydrate oxidative capacity, and inhibit the progression of type 2 diabetes. The combination of the punicic acid and cannabinoids can enhance the immune response and treat disorders in the immune system and gastrointestinal tract as well as promote the development and function of the immune system and prevent of metabolic disorders. Further, the combination of the punicic acid and cannabinoids can be useful against the proliferation and survival of human breast adenocarcinoma (MCF-7) cells and skin cancer. The combination of the punicic acid and cannabinoids can reduce anxiety, help control nausea and vomiting caused by chemotherapy, aid in the destruction of cancer cells, slow tumor growth, help relax tight muscles in people with multiple sclerosis, reduce inflammation, provide pain relief, stimulate appetite, improve weight gain in people with undergoing certain medical treatments, and contribute to an increased health benefit towards cardiovascular conditions. The combination of the punicic acid and cannabinoids can be used in the treatment of anxiety and depression and can also provide neuroprotective benefits. Historically, anxiety and depression have been treated with pharmaceutical drugs, that are known to cause severe side effects including drowsiness, agitation, insomnia, sexual dysfunction and headache. Significantly, the combination of the punicic acid and cannabinoids can be used to safely treat not only insomnia, anxiety and depression, but also to relieve such conditions as agitation, insomnia, inflammation, sexual dysfunction and headache.

In addition to punicic acid and cannabinoids, the compositions of the invention can optionally include a number of other biologically active compounds.

One such biologically active compound is abscisic acid ("ABA"). Abscisic acid, as used herein, can refer to any one or more, in any combination, of abscisic acid free acid form, esters thereof, pharmaceutically suitable salts thereof, metabolites thereof, structurally related compounds thereof, and analogs thereof. ABA is a widely studied naturally occurring phytohormone that plays a key role in many different processes in plants, including stress response, leaf abscission, growth and development, and germination. ABA is also a key component of sugar sensitivity, as plants deficient of ABA are glucose insensitive. While ABA is ubiquitously found in plants, and often consumed by humans as a part of the daily diets, its natural content ranges from 5-15 mg/kg in leaves.

Researchers recognized the effect of ABA on mammalian glucose homeostasis based upon the structural similarities between ABA and the thiazolidinedione (TZD) class of insulin-sensitizing antidiabetic drugs, which bind to the ligand-binding domain of the transcription factor PPARγ and activate the transcription of several genes involved in glucose and lipid metabolism. ABA was shown to have similar efficacy to that of TZDs in mouse models of diabetes, and exerts glucose-normalizing effects when administered to genetically obese mice fed a high-fat diet and to mice with diet-induced obesity. ABA is an endogenous regulator of glucose disposal in mammals. Specifically, dietary ABA has been found to alleviate fasting blood glucose and glucose tolerance during a glucose tolerance test. It has also been found that adipocyte hypertrophy, tumor necrosis factor-α (TNF-α) expression, and macrophage infiltration were significantly attenuated in ABA-fed mice. Because ABA is naturally present in our diet, it provides a natural baseline to balance glucose levels in healthy individuals and manage glycemic control in prediabetic, diabetic, and metabolic syndrome patients, and indicates that ABA can be used as a nutritional and pharmaceutical intervention against diabetes, and in particular Non-Insulin Dependent Diabetes Mellitus, and against inflammation, including obesity-related inflammation. Notably, there are no preventative medications currently available to the latter group. Additionally, ABA can be useful for treating chronic diseases such as atherosclerosis and inflammatory bowel disease. ABA is naturally present in our diet thereby providing a natural way to balance glucose levels in healthy individuals and manage glycemic control in prediabetic, diabetic, and metabolic syndrome patients. In embodiments of the functional beverage as described herein, ABA is used as a component of a multi-functional beverage. In some embodiments, ABA is provided in the compositions of the invention in the form of one or more of fig extract, banana extract, bilberry extract, avocado extract, and apricot extract. In other embodiments, the ABA is provided as purified abscisic acid free acid form, esters thereof, pharmaceutically suitable salts thereof, metabolites thereof, structurally related compounds thereof, and analogs thereof.

Additional biologically active compounds that can be included in the compositions of the invention include fiber supplements, sleep enabling supplements (melatonin), and supplements that increase metabolic intensity (such as found in, for example, some energy drinks) or promote satiety/weight loss. Such weight loss compounds include, but are not limited to, satiety inducing compounds and fat uptake inhibitors such as proteinase inhibitor II, green coffee bean extract, chlorogenic acid, green tea leaf extract, caffeine, theophylline, polyphenols, ashwagandha extract, pinolenic acid, hoodia, chitosan, chromium picolinate, conjugated linoleic acid, glucomannan, green tea extract, guar gum, guarana, guggal, senna, ephedra, bitter orange, fucoxanthin, white bean extract, vitamin D, human chorionic gonadotropin, resveratrol, capsaicin, chia, hoodia, L-carnitine, raspberry ketones, banana leaf, red clover, ginger, almonds, acai berry, flax seeds, leucine, lipodrene, thylakoids, and thylakoid extracts.

Other biologically active compounds that can be included in the compositions of the invention include amino acids. Exemplary amino acids include comprising alpha galactosidase, amylase, bromelain, cellulase, papain, peptidase, protease, proteolytic enzymes, superoxide dismutase, trypsin, betaine, casein, glutamic acid, L-alanine, L-arginine, L-cysteine, L-glutamine, L-glycine, L-histidine, L-isoleucine, L-leucine, L-lysine, L-methionine, L-ornithine, L-phenylalanine, L-proline, L-taurine, L-threonine, L-tryptophan, L-tyrosine, L-valine, N-acetyl-L-cysteine, protein soluble soy, soy protein isolates, and whey protein isolates.

Other biologically active compounds that can be included in the compositions of the invention are antioxidants. Exemplary antioxidants include neoflavonals, tocopherol, tocotrienol, lipoic acid, melatonin, superoxide dismutase, coenzyme Q10, alpha lipoic acid, vitamin A, chromium biotin, selenium, and ascorbic acid.

Other biologically active compound that can be included in the compositions of the invention are carotenoids. Exemplary carotenoids include α-carotene, β-carotene, γ-carotene, δ-carotene, ε-carotene, lycopene, cryptoxanthin, lutein, zeaxathin, apocarotenal astaxanthin, canthaxanthin, and lutein/lutein esters.

Other biologically active compounds that can be included in the compositions of the invention include flavonoids. As used herein, a "flavonoid" or "bioflavonoid" refers to flavones, isoflavanoids and neoflavanoids, subclasses, subgroups, and chemically related compounds thereof, including flavanols, as used and defined according to IUPAC nomenclature and designation. The flavonoid can be any one or more of esveratrol, quercetin, rutin, catechin, epicatechin, epigallocatechin, epigallocatechin gallate, and proanthocyanidin.

Other biologically active compounds that can be included in the compositions of the invention include isoflavones. Exemplary isoflavones include genistein, daidzein, biochanin A, and formononetin.

In some versions, the compositions of the invention can include one or more vitamins. Exemplary vitamins include vitamin A, vitamin $B_1$, vitamin $B_2$, vitamin $B_3$, vitamin $B_5$, vitamin $B_6$, vitamin $B_9$, vitamin $B_{12}$, vitamin C, vitamin $D_3$, vitamin E, vitamin $K_1$, vitamin $K_2$, and vitamin H (biotin). In some versions, the compositions of the invention can include one or more minerals. Exemplary minerals include boron, calcium, chloride, chromium, cobalt, copper, fluorine, iodine, iron, magnesium, manganese, molybdenum, nickel, phosphorous, potassium, selenium, silicon, sodium, strontium, sulfur, vanadium, and zinc. In some versions, the concentrations of each of the vitamins and minerals can be at least about 0.1% (w/w), at least about 0.01% (w/w), at least about 0.001% (w/w), at least about 0.0001% (w/w), at least about 0.00001% (w/w), at least about 0.000001% (w/w), at least about 0.0000001% (w/w), or at least about 0.00000001% (w/w) of the final mass of the composition. In some versions, the concentrations of each of the vitamins and minerals can be less than about 1% (w/w), less than about 0.1% (w/w), less than about 0.01% (w/w), less than about 0.001% (w/w), less than about 0.0001% (w/w), less than about 0.00001% (w/w), less than about 0.000001% (w/w), less than about 0.0000001% (w/w), or less than about 0.00000001% (w/w) of the final mass of the composition. In some versions, the compositions can include vitamins $B_6$, $B_{12}$, C, D, and/or E, formulated to 10% RDI (each) per serving based on a 2000 calorie diet.

The functional beverage compositions provided herein utilize various biologically active components that are not easily solvated in an aqueous medium. Therefore, certain chemical compositions, such as certain emulsifiers and stabilizers, are added to solubilize those biologically active compounds. In some embodiments, the functional beverage is generally comprised of natural emulsifiers and stabilizers or emulsifiers and stabilizers that are extracted, isolated and/or concentrated from natural sources. In certain embodiments the functional beverage is comprised of a solvating agent to solvate a non-polar or non-aqueous fluid. In other certain embodiments, the solvating agent is an emulsifier. In certain embodiments the emulsifier is at least one phospholipid. In specific embodiments the phospholipid is one or more of soy lecithin, rapeseed lecithin, corn or sunflower lecithins, egg lecithin, Epicorn 200, Phosal 50 PG, dioleyl phospatidylcholine (DOPC), oleyl palmytoyl phosphatidylcholine (POPC), and the corresponding serines, ethanol amines, glycerol, and others, may be used. According to such embodiments, the formulation may comprise an emulsifier and/or stabilizer between about 0.0001% (v/v) and about 1.0% (v/v), between about 0.0001% (v/v) and about 0.1% (v/v), between about 0.0001% (v/v) and about 0.01% (v/v), between about 0.0001% (v/v) and about 0.001% (v/v) of a final volume of the multi-functional beverage composition.

Some versions of the invention provide functional beverage compositions in liquid form. The functional beverage compositions can comprise water, lecithin, a punicic acid-containing oil comprising punicic acid, and a cannabinoid-containing oil comprising cannabinoid.

In some versions, the water is present in the composition in an amount of at least about 90% w/v, at least about 91% w/v, at least about 92% w/v, at least about 93% w/v, at least about 94% w/v, at least about 95% w/v, at least about 96% w/v, at least about 97% w/v, at least about 98% w/v, at least about 99% w/v, at least about 99.1% w/v, at least about 99.2% w/v, at least about 99.3% w/v, at least about 99.4% w/v, at least about 99.5% w/v, at least about 99.6% w/v, at least about 99.7% w/v, at least about 99.8% w/v, at least about 99.9% w/v.

Exemplary lecithins include rapeseed lecithin, soy lecithin, sunflower lecithin, corn lecithin, egg lecithin, dioleyl phosphatidylcholine, oleyl palmitoyl phosphatidylcholine, and derivatives thereof. In some versions, lecithin is present in the composition in an amount of at least about 0.0001% w/v, at least about 0.0005% w/v, at least about 0.001% w/v, at least about 0.005% w/v, or about 0.01% w/v. In some versions, the lecithin is present in the composition in an amount up to about 0.05% w/v, up to about 0.1% w/v, up to about 0.5% w/v, up to about 1% w/v, or up to about 5% w/v.

The punicic acid-containing oil can include any oil or mixture of oils comprising punicic acid. In some versions, the punicic acid-containing oil is pomegranate seed oil.

In some versions, the punicic acid-containing oil comprises punicic acid in an amount of at least about 1% w/v, at least about 5% w/v, at least about 10% w/v, at least about 15% w/v, at least about 20% w/v, at least about 25% w/v, at least about 30% w/v, at least about 35% w/v, at least about 40% w/v, at least about 45% w/v, at least about 50% w/v, at least about 55% w/v, at least about 60% w/v, at least about 75% w/v, at least about 80% w/v, at least about 90% w/v, or at least about 95% w/v. In some versions, the punicic acid-containing oil comprises punicic acid in an amount up to about 5% w/v, up to about 10% w/v, up to about 15% w/v, up to about 20% w/v, up to about 25% w/v, up to about 30% w/v, up to about 35% w/v, up to about 40% w/v, up to about 45% w/v, up to about 50% w/v, up to about 55% w/v, up to about 60% w/v, up to about 75% w/v, up to about 80% w/v, up to about 90% w/v, up to about 95% w/v, or up to about 99% w/v. The punicic acid in the punicic acid-containing oil can be in any form, including free-acid form, salt form, or esterified (e.g., glyceride) form.

In some versions, the punicic acid-containing oil is present in the composition in an amount of at least about 0.0001% w/v, at least about 0.0005% w/v, at least about 0.001% w/v, at least about 0.005% w/v, or about 0.01% w/v. In some versions, the punicic acid-containing oil is present in the composition in an amount up to about 0.05% w/v, up to about 0.1% w/v, up to about 0.5% w/v, up to about 1% w/v, or up to about 5% w/v.

The cannabinoid-containing oil can include any oil or mixture of oils comprising cannabinoid. In some versions, the cannabinoid-containing oil is a hemp oil. In some versions, the cannabinoid-containing oil is full-spectrum hemp oil. "Full-spectrum hemp oil" as used herein refers to oil extracted from hemp without selective purification or removal of specific cannabinoids from the oil. Full-spectrum hemp oil therefore contains all or substantially all of the same cannabinoids and compounds found in the oil of the original hemp plant from which the oil is extracted.

In some versions, the cannabinoid-containing oil comprises cannabinoid in an amount of at least about 1% w/v, at least about 5% w/v, at least about 10% w/v, at least about 15% w/v, at least about 20% w/v, at least about 25% w/v, at least about 30% w/v, at least about 35% w/v, at least about 40% w/v, at least about 45% w/v, at least about 50% w/v, at least about 55% w/v, at least about 60% w/v, at least about 75% w/v, at least about 80% w/v, at least about 90% w/v, or at least about 95% w/v. In some versions, the cannabinoid-containing oil comprises cannabinoid in an amount up to about 5% w/v, up to about 10% w/v, up to about 15% w/v, up to about 20% w/v, up to about 25% w/v, up to about 30% w/v, up to about 35% w/v, up to about 40% w/v, up to about 45% w/v, up to about 50% w/v, up to about 55% w/v, up to about 60% w/v, up to about 75% w/v, up to about 80% w/v, up to about 90% w/v, up to about 95% w/v, or up to about 99% w/v.

In some versions, the cannabinoid-containing oil comprises cannabidiol in an amount of at least about 1% w/w, at least about 5% w/w, at least about 10% w/w, at least about 15% w/w, at least about 20% w/w, at least about 25% w/w, at least about 30% w/w, at least about 35% w/w, at least about 40% w/w, at least about 45% w/w, at least about 50% w/w, at least about 55% w/w, at least about 60% w/w, at least about 75% w/w, at least about 80% w/w, at least about 90% w/w, or at least about 95% w/w. In some versions, the cannabinoid-containing oil comprises cannabidiol in an amount up to about 5% w/w, up to about 10% w/w, up to about 15% w/w, up to about 20% w/w, up to about 25% w/w, up to about 30% w/w, up to about 35% w/w, up to about 40% w/w, up to about 45% w/w, up to about 50% w/w, up to about 55% w/w, up to about 60% w/w, up to about 75% w/w, up to about 80% w/w, up to about 90% w/w, up to about 95% w/w, or up to about 99% w/w.

In some versions, the cannabinoid-containing oil is present in the composition in an amount of at least about 0.0001% w/v, at least about 0.0005% w/v, at least about 0.001% w/v, at least about 0.005% w/v, or at least about 0.01% w/v. In some versions, cannabinoid-containing oil is present in the composition in an amount up to about 0.01% w/v, up to about 0.05% w/v, up to about 0.1% w/v, up to about 0.5% w/v, up to about 1% w/v, or up to about 5% w/v.

In some versions, the composition comprises no more than about 0.00001% w/v, no more than about 0.00005% w/v, no more than about 0.0001% w/v, no more than about 0.0005% w/v, no more than about 0.001% w/v, no more than about 0.005% w/v, no more than about 0.01% w/v, no more than about 0.05% w/v, or no more than about 0.1% w/v of total non-lecithin emulsifiers and stabilizers. In some versions, the composition comprises at least about 0.0001% w/v, at least about 0.0001% w/v, at least about 0.0005% w/v, at least about 0.001% w/v, at least about 0.005% w/v, at least about 0.01% w/v, or at least about 0.05% w/v of total non-lecithin emulsifiers and stabilizers. The phrase "non-lecithin emulsifiers and stabilizers" refers to any and all emulsifiers and stabilizers present in the composition other than lecithin. The terms "emulsifiers" and "stabilizers" are well-known in the art. Examples of non-lecithin emulsifiers and stabilizers include xanthan gum, polysorbate, propylene glycol, and distilled acetylated monoglycerides, among others.

In some versions, the composition comprises no more than about 0.00001% w/v, no more than about 0.00005% w/v, no more than about 0.0001% w/v, no more than about 0.0005% w/v, no more than about 0.001% w/v, no more than about 0.005% w/v, no more than about 0.01% w/v, no more than about 0.05% w/v, or no more than about 0.1% w/v of polysaccharides. In some versions, the composition comprises no more than about 0.00001% w/v, no more than about 0.00005% w/v, no more than about 0.0001% w/v, no more than about 0.0005% w/v, no more than about 0.001% w/v, no more than about 0.005% w/v, no more than about 0.01% w/v, no more than about 0.05% w/v, or no more than about 0.1% w/v of branched-chain polysaccharides. In some versions, the composition comprises no more than about 0.00001% w/v, no more than about 0.00005% w/v, no more than about 0.0001% w/v, no more than about 0.0005% w/v, no more than about 0.001% w/v, no more than about 0.005% w/v, no more than about 0.01% w/v, no more than about 0.05% w/v, or no more than about 0.1% w/v of xanthan gum. In some versions, the composition is devoid of polysaccharides. In some versions, the composition is devoid of branched-chain polysaccharides. In some versions, the composition is devoid of xanthan gum.

In some versions, the lecithin comprises at least about 5% w/w, at least about 10% w/w, at least about 15% w/w, at least about 20% w/w, at least about 25% w/w, at least about 30% w/w, at least about 35% w/w, at least about 40% w/w, at least about 45% w/w, at least about 50% w/w, at least about 55% w/w, or at least about 60% w/w of all emulsifiers and stabilizers present in the composition.

In some versions, the composition further comprises alcohol. In some versions the alcohol is present in the composition in an amount of at least about 0.0001% w/v, at least about 0.0005% w/v, at least about 0.001% w/v, at least about 0.005% w/v, at least about 0.01% w/v, at least about 0.05% w/v, at least about 0.1% w/v, at least about 0.5% w/v, at least about 1% w/v, at least about 5% w/v, at least about 10% w/v. In some versions, the alcohol is present in the composition in an amount up to about 0.05% w/v, up to about 0.1% w/v, up to about 0.5% w/v, up to about 1% w/v, or up to about 5% w/v. Exemplary alcohols include ethanol. The alcohol can include compounds dissolved therein, including, for example, flavorings.

In some versions, the composition further comprises citric acid. In some versions the citric acid is present in the composition in an amount of at least about 0.0001% w/v, at least about 0.0005% w/v, at least about 0.001% w/v, at least about 0.005% w/v, at least about 0.01% w/v, at least about 0.05% w/v, at least about 0.1% w/v, at least about 0.5% w/v, at least about 1% w/v, at least about 5% w/v, at least about 10% w/v. In some versions, the citric acid is present in the composition in an amount up to about 0.05% w/v, up to about 0.1% w/v, up to about 0.5% w/v, up to about 1% w/v, or up to about 5% w/v. The citric acid can help to stabilize the pH of the composition and can add to the flavor profile.

In some versions, the composition is carbonated. In some versions, the composition can comprise at least about 0.01 volumes, at least about 0.05 volumes, at least about 0.1 volumes, at least about 0.5 volumes, at least about 1 volume, at least about 1.5 volumes, at least about 2 volumes, at least about 2.5 volumes, at least about 3 volumes, at least about 3.5 volumes, at least about 4 volumes, at least about 4.5 volumes, or at least about 5 volumes of dissolved $CO_2$. In some versions, the composition can comprise up to about 0.05 volumes, up to about 0.1 volumes, up to about 1 volume, up to about 1.5 volumes, up to about 2 volumes, up to about 2.5 volumes, up to about 3 volumes, up to about 3.5 volumes, up to about 4 volumes, up to about 4.5 volumes, up to about 0.5 volumes, or up to about 5 volumes of dissolved $CO_2$. Volume of dissolved $CO_2$ refers to the volume $CO_2$ would take up at a pressure of one atmosphere (about 15 pounds per square inch) and a temperature of 0° C. (32° F.) (standard temperature and pressure) relative to the volume of the beverage in which the $CO_2$ is dissolved.

In preferred versions of the compositions of the invention, any oil in the composition, which includes the punicic acid-containing oil, the cannabinoid-containing oil, and any other oil comprised within the composition, are stably suspended within the water. "Stably suspended" in this context means that at least 80% w/w of the oil in the composition is suspended within the water, as opposed to floating as a separate phase on the surface of the water or separating as a separate phase from the water, for a period of time of at least 1 day. In various versions, at least about 85% w/w of the oil, at least about 87% w/w of the oil, at least about 90% w/w of the oil, at least about 95% w/w of the oil, at least about 96% w/w of the oil, at least about 97% w/w of the oil, at least about 98% w/w of the oil, at least about 99% w/w of the oil, or at least about 99.5% w/w of the oil in the composition is suspended within the water, as opposed to floating as a separate phase on the surface of the water or separating as a separate phase from the water, for a period of time of at least 1 day, at least about 30 days, at least about 90 days, or at least about one year. In some versions of the invention, less than about 70% w/w, less than about 75% w/w, less than about 80% w/w, less than about 85% w/w, less than about 90% w/w, less than about 93% w/w, less than about 95% w/w, less than about 96% w/w, less than about 97% w/w, less than about 98% w/w, less than about 99% w/w, or less than about 99.5% of the oil (e.g., the combination of the punicic acid-containing oil and the cannabinoid-containing oil) is present as a separate, non-suspended phase on the surface of the remaining composition for a time period of at least about 1 day, at least about 30 days, at least about 90 days, or at least about one year. Such metrics can be determined by collecting any oil floating on the surface of the water (or otherwise separated from the water), determining the mass of the collected oil, and calculating the proportion of the mass of the collected oil as a percentage of the mass of the total oil added to the composition during its production.

Methods of making the compositions of the invention are also provided herein. Some methods include any one or more of the following steps: providing a sub-volume of water, wherein the sub-volume is less than a final composition volume; adding lecithin to the sub-volume of water to generate a lecithin-water mixture; incubating the lecithin-water mixture; mixing a punicic acid-containing oil comprising punicic acid and a cannabinoid-containing oil comprising cannabinoid to generate an oil mixture; adding the oil mixture to the lecithin-water mixture to generate an oil-in-water emulsion; adding water to the oil-in-water emulsion in an amount to increase the volume of the oil-in-water emulsion to the final composition volume, thereby generating a full-volume oil-in-water emulsion; and carbonating the full-volume oil-in-water emulsion.

In some versions, the sub-volume of water has a volume of at least about 1% v/v, at least about 5% v/v, at least about 10% v/v, at least about 15% v/v, at least about 20% v/v, at least about 25% v/v, at least about 30% v/v, at least about 35% v/v, at least about 40% v/v, at least about 45% v/v, at least about 50% v/v, at least about 55% v/v, at least about 60% v/v, at least about 75% v/v, at least about 80% v/v, at least about 90% v/v, or at least about 95% v/v of the final composition volume. In some versions, the sub-volume of water has a volume up to about 5% v/v, up to about 10% v/v, up to about 15% v/v, up to about 20% v/v, up to about 25% v/v, up to about 30% v/v, up to about 35% v/v, up to about 40% v/v, up to about 45% v/v, up to about 50% v/v, up to about 55% v/v, up to about 60% v/v, up to about 75% v/v, up to about 80% v/v, up to about 90% v/v, up to about 95% v/v, or up to about 99% v/v of the final composition volume.

The lecithin can be added to the sub-volume of water in an amount by weight sufficient to provide any of the concentrations described above for the composition of the invention when the composition is brought to the final composition volume.

The lecithin-water mixture can be incubated for a time of at least about 30 seconds, at least about 1 minute, at least about 2 minutes, at least about 3 minutes, at least about 4 minutes, at least about 5 minutes, at least about 10 minutes, or at least about 15 minutes.

The punicic acid-containing oil in the oil mixture can be added to the lecithin-water mixture in an amount by weight sufficient to provide any of the concentrations described above for the composition of the invention when the composition is brought to the final composition volume. In some versions, the punicic acid-containing oil is or comprises pomegranate seed oil.

The cannabinoid-containing oil in the oil mixture can be added to the lecithin-water mixture in an amount by weight sufficient to provide any of the concentrations described above for the composition of the invention when the composition is brought to the final composition volume. In some versions, the cannabinoid-containing oil is or comprises full spectrum hemp oil.

Some versions further include adding alcohol to the oil-in-water emulsion. The alcohol can be added to the oil-in-water emulsion in an amount by weight sufficient to provide any of the concentrations described above for the composition of the invention when the composition is brought to the final composition volume. Exemplary alcohols include ethanol. The alcohol can include compounds dissolved therein, including, for example, flavorings. The alcohol can be added to the oil-in-water emulsion prior to carbonating the oil-in-water emulsion.

Some versions further include adding citric acid to the oil-in-water emulsion. The citric acid can be added to the oil-in-water emulsion in an amount by weight sufficient to provide any of the concentrations described above for the composition of the invention when the composition is brought to the final composition volume. The citric acid can be added to the oil-in-water emulsion after adding alcohol to the oil-in-water emulsion. The citric acid can be added to the oil-in-water emulsion prior to carbonating the oil-in-water emulsion.

The full-volume oil-in-water emulsion can be carbonated to any of the concentrations described above for the composition of the invention when the composition is brought to the final composition volume.

Some versions further include pasteurizing the full-volume oil-in-water emulsion. An exemplary method of pasteurization is tunnel pasteurization.

The functional beverage compositions described herein are contemplated to provide a functional benefit to a consumer (a "functional beverage" and/or a "functional food"). Such functional beverages are formulated to provide an important nutritive food source that contributes to the prevention, management and/or treatment of chronic diseases and/or maintenance of a healthy state. This benefit can be provided to a consumer when new ingredients or more of an existing ingredient are added to a beverage so that an added health benefit is gained. Applications for the use of functional beverages as described herein include, but are not limited to, the prevention, management and/or treatment of unhealthy blood glucose levels, gut health, immune system response, and neurological conditions. Additionally, the use of functional beverages as described herein can be for the maintenance of healthy conditions related to gut/digestive health, blood glucose levels, immune system response, and neurological/emotional conditions. The compositions of the invention can also or alternatively be used to reduce inflammation in any of a number of disease states, including inflammatory bowel disease and diabetes.

The compositions of the invention can be used for the treatment of a wide range of intestinal health applications. These applications include general gut health maintenance and disorder prevention, as well as to specifically treat conditions including, but not limited to, diarrhea, Traveler's Diarrhea, antibiotic-associated diarrhea, inflammatory bowel disease, excessive stomach acid, dyspepsia, constipation, irritable bowel syndrome, Crohn's Disease, lactose intolerance, and pathogenic infection. Additional uses of the compositions of the invention include increased antioxidant activity, an anti-inflammatory composition, improving glucose uptake/decreasing insulin resistance, nephroprotective activity, improving memory, weight loss, and anti-cancer activity. Therefore, the present invention provides for preventive and/or therapeutic compositions for treating diseases and conditions or maintaining the health of individuals as relates to intestinal health.

Lifestyle and diet both can affect fluctuations in blood glucose levels, leading to a number of health complications and risks. For example, a lack of sufficient amount of sleep is known to cause elevated blood glucose levels. When under stress, especially continuous levels, the body produces hormones that attenuate normal insulin levels, thereby affecting blood glucose levels. Diets high in saturated fats and carbohydrates severely affect both body weight as well as blood sugar levels. Notably, added processed sugars contribute significantly to weight gain as well as blood glucose levels. Even with widespread education, many consumers today still maintain lifestyles with significant levels of stress, sleeplessness and diets high in fats and excess sugars, leading to widespread obesity. In fact, according to estimates by the CDC, in the year 2000 30% of Americans were categorically obese and 65% overweight, with those numbers continuing to rise.

One of the manifestations associated with this obesity epidemic is the growing number of people diagnosed with Non-Insulin Dependent Diabetes Mellitus (NIDDM) characterized by insulin resistance and inflammation that can lead to multiple serious disease states. It has been recently estimated that 21 million Americans had NIDDM and 40% of middle-aged adults had prediabetes, a condition characterized by either impaired glucose tolerance or high blood fasting glucose concentrations. Future predictions indicate that 33% of children born in 2000 will eventually become diabetic. The impending consequence is that millions of people, if not already, will soon become dependent on oral antidiabetic medications to maintain their quality of life.

A need also exists for novel methods of treating or preventing disorders such as diabetes, including Type 2 diabetes. In western societies, the high prevalence of obesity results in several metabolic disorders such as Type 2 diabetes, cardiovascular disease, hypertension, and hyperlipemia. Approximately 15 million Americans are afflicted by Type 2 diabetes. Current treatments for Type 2 diabetes include agonists of peroxisome proliferator-activated receptor gamma such as thiazolidinediones (TZDs). However, questions have been raised regarding the safety of these treatments due to adverse cardiovascular (fluid retention and congestive heart failure) and liver (fatty liver) side effects. The functional beverages and uses as described herein provide methods of preventing or treating Metabolic Syndrome, diabetes, Type 1 diabetes, Type 2 diabetes, and obesity, including nutritional methods that act upon molecular networks located in the interface between immunity, inflammation, and metabolism.

The compositions provided herein can be used as preventive and/or therapeutic compositions for treating diseases and conditions or maintaining the health of individuals as relates to blood sugar level control. The compositions described herein can increase the effective delivered concentration of such useful functional ingredients which aid in the control or maintenance of blood glucose level, and can be formulated as a daily dietary supplement, preventative treatment or for clinical applications treating systemic or chronic disease states and disorders.

The compositions provided herein can also be used as preventive and/or therapeutic compositions for treating diseases and conditions or maintaining the mental, emotional and/or neurological health of individuals. The compositions provided herein increase the effective delivered concentration of such useful functional ingredients such as cannabinoids, which aid in the control or maintenance of mental, emotional and/or neurological health, and can be formulated as a daily dietary supplement, preventative treatment or for clinical applications treating systemic or chronic disease states and disorders.

A key aspect of many disease states involves the body's immune response. The immune system functions are complicated processes that involve the coordinated efforts of several types of cells and tissues. Due to the complexity of the body's immune response, continuing studies shed light on ways to bolster the immune system to enhance the immune response of an animal. Ideally, new methods and compositions as provided herein enhance the natural activity level of the immune system and/or will act to prevent or attenuate adverse side effects associated with immune and/or inflammatory responses. The immune response is the body's mechanism of defense against foreign substances that invade to cause infection and/or disease. Compromised immune systems or autoimmune responses may impact multiple aspects of health, including intestinal health, disease states from infections, cardiovascular health, mental/emotional health, etc. The immune system's functions are complicated processes that involve the coordinated efforts of several types of cells and cellular proteins, including, but not limited to, white blood cells, B-cells, T-cells (a subpopulation of white blood cells) and their cytokines (such as interleukin-1 (IL-1), interleukin-2 (IL-2), gamma interferon (IFN-γ) and tumor necrosis factor (TNF) Due to the complexity of the body's immune response, ongoing research will reveal novel ways to bolster the immune system to enhance the immune response of an animal and characterize the effectiveness of biologically active compounds in improving immunity or preventing or attenuating adverse side effects associated with immune and/or inflammatory responses. The compositions provided herein can be used as a multi-faceted approach to improved immune response for activity against a variety of health conditions or for preventative maintenance of a healthy condition. The compositions can be effective against or provide support for a number of immunity related conditions. As exemplified below, the combined effect of punicic acid with cannabinoids can have a synergistic effect on the immune response. The functional beverage compositions described herein increase the effective delivered concentration of such useful functional ingredients that aid in the control or maintenance of immune health and function, and can be formulated as a daily dietary supplement, preventative treatment or for clinical applications treating systemic or chronic disease states and disorders.

One particular aspect of the invention directed to methods of decreasing inflammation in a subject. The methods comprise administering a composition comprising punicic acid and a cannabinoid in amounts effective to decrease inflammation in the subject. In some versions, the composition comprises punicic acid and a cannabinoid in amounts synergistically effective to decrease inflammation in the subject. In some versions, the subject is a subject suffering from an inflammatory disorder. In some versions, the subject is a subject suffering from a condition selected from the group consisting of irritable bowel disease and diabetes. In some versions, the punicic acid and the cannabinoid are present in the composition in amounts effective to maintain or increase glucose uptake in CD4+ T-cells compared to a composition comprising the cannabinoid and lacking the punicic acid but otherwise identical to the composition comprising the punicic acid and the cannabinoid. In preferred versions, the composition is a functional beverage composition as described herein.

The invention also provides methods for maintaining or improving digestive health. The methods comprise administering to a subject in need thereof a functional beverage composition of the invention. The functional beverage composition can be administered in an amount sufficient to provide relief from gastrointestinal bloating of an individual.

The invention also provides methods for the prevention and treatment of a gastrointestinal disorder. The methods comprise administering to a subject in need thereof a functional beverage composition of the invention. The gastrointestinal disorder can comprise one or more of diarrhea, Traveler's Diarrhea, antibiotic-associated diarrhea, inflammatory bowel disease, excessive stomach acid, dyspepsia, constipation, irritable bowel syndrome, Crohn's Disease, non-allergenic food hypersensitivity, lactose intolerance, and pathogenic infection.

The invention also provides methods for the treatment of a systemic disorder. The methods comprise administering to a subject in need thereof a functional beverage composition of the invention. The systemic disorder can comprise any one or more of pain-associated disorders, inflammatory disorders and conditions, appetite suppression or stimulation, symptoms of vomiting and nausea, disorders and conditions associated with anxiety, disorders and conditions associated with psychosis, disorders and conditions associated with seizures and/or convulsions, sleep disorders and conditions, elevated cholesterol, elevated blood glucose levels, dietary intolerances, hypertension, acid reflux disease, colon cancer, and obesity.

The invention also provides methods for improving immune response in a subject. The methods comprise administering to the subject a functional beverage composition of the invention. Improving the immune response can further comprise lowering the severity of at least one of the group consisting of diarrhea, inflammatory bowel disease, Crohn's disease, ulcerative colitis, excessive stomach acid, dyspepsia, and pathogenic infection.

The invention also provides methods for increasing glucose tolerance, increasing insulin sensitivity, and/or improving obesity-induced inflammation in a mammal. The methods comprise to a subject in need thereof a functional beverage composition of the invention.

The invention also provides methods for the treatment of irritable bowel syndrome, irritable bowel disease, or diabetes. The methods comprise administering to a subject in need thereof a functional beverage composition of the invention.

U.S. Provisional Application 62/788,397 is incorporated herein by reference in its entirety. In case of conflicts between U.S. Provisional Application 62/788,397 and the present document, the present document controls.

Percent w/v refers to an amount of a substance in g/100 mL.

The elements and method steps described herein can be used in any combination whether explicitly described or not.

All combinations of method steps as used herein can be performed in any order, unless otherwise specified or clearly implied to the contrary by the context in which the referenced combination is made.

As used herein, the singular forms "a," "an," and "the" include plural referents unless the content clearly dictates otherwise.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All patents, patent publications, and peer-reviewed publications (i.e., "references") cited herein are expressly incorporated by reference to the same extent as if each individual reference were specifically and individually indicated as being incorporated by reference. In case of conflict between the present disclosure and the incorporated references, the present disclosure controls.

It is understood that the invention is not confined to the particular construction and arrangement of parts herein illustrated and described, but embraces such modified forms thereof as come within the scope of the claims.

EXAMPLES

Functional Beverage Compositions and Methods of Making Same

Figure 2:
Figure 3:
FIGS. 3 and 4 show results of vigorously mixing water and cannabidiol (CBD).
Figure 4:

Pomegranate seed oil and cannabidiol (CBD) are both non-polar compounds and do not mix completely with polar compounds to form a stable solution, even under vigorous mixing. Over time, the non-polar compounds will aggregate together and fall out of aqueous suspension. FIG. 1 shows the result of water and pomegranate seed oil after being mixed vigorously. The resulting layer of pomegranate seed oil can be identified on the surface of the water. FIG. 2 shows a small amount of pomegranate seed oil temporarily remaining in suspension after mixing, causing a slight haze in the solution. FIG. 3 shows the result of CBD and water after being mixed vigorously, wherein a buoyant, non-dissolving solid remains floating on top of the water. FIG. 4 shows the clarity of the solution after mixing, with no visible suspension able to be detected. Beverages manufactured with only polar and non-polar substances would behave and result in a composition having an immiscible and undesirable tactile quality; pomegranate seed oil mixed with water is likely to result in a fatty or oily layer on top of the water, or with CBD, the water surface peppered with crystalline flakes. In most cases, the non-polar components are likely to adhere to the sides of the container.

Figure 5:
FIGS. 5 and 6 show results of vigorously mixing water, pomegranate seed oil, and CBD.
Figure 6:

For broad-based consumer success, it is desirable that a functional beverage product consistent in flavor, quality, and mouthfeel be manufacturable using an easily replicated process, and be food-safe. Immiscible components can result in material floating on the surface of the beverage, wherein the immiscible materials can shelter can promote the growth of contaminating organisms or provide localized regions survivable from pasteurizing temperatures. Additionally, such immiscible components can become a choking hazard to the unaware consumer. Non-polar compounds mix well with other non-polar compounds. FIG. 5 shows the successful dissolving of CBD within pomegranate seed oil, even at refrigeration temperatures. However, when the CBD and pomegranate seed oil are mixed vigorously with water, a cloudy oil layer aggregates on the surface of the water, indicating that both pomegranate seed oil and CBD remain immiscible in the water. FIG. 6 shows the slightly increased haze from the loosely suspended pomegranate seed oil-CBD mixture; this suspension will eventually settle out and aggregate on the surface.

Emulsions can be complete or incomplete: a complete emulsion is one where the non-polar and polar phases are evenly and permanently combined; an incomplete emulsion is one that is likely, with time, to settle out into respective immiscible portions. Complete emulsions are typically achieved using an emulsifying agent or compound. Such a compound can exhibit polar and non-polar distal portions which will bind, respectively, to a non-polar substance on one end of a molecule and a polar substance on the distal end of the molecule, thereby allowing for the polar and non-polar substances to be miscible. An incomplete emulsion can result from shaking, stirring, or otherwise agitating a solution, breaking up one liquid substance into successively smaller droplets and suspending the now-tiny droplets of that substance within the other. By way of example, the "haze" as shown in FIG. 6 is shown the result of small oil droplets that have been shaken into solution. The smaller the oil droplet size, the longer the time required for the incomplete emulsion to reverse and separate again into immiscible components. For the functional beverage compositions provided herein, dissolved carbon dioxide, non-polar gas, is used reduce the oil droplet size considerably. Additionally, the specific vitamin blend used herein contains a blend of encapsulated fat soluble and water-soluble vitamins that, while providing for fortifying nutritional supplements, also increases the population of micro droplets formed.

Carbohydrate stabilizers are typically complex carbohydrate chains that act as thickeners and gelling agents. Carbohydrate stabilizers can impede the motion of oil droplets in solution to impede their aggregation. Xanthan gum is an example of a carbohydrate stabilizer.

Figure 7:
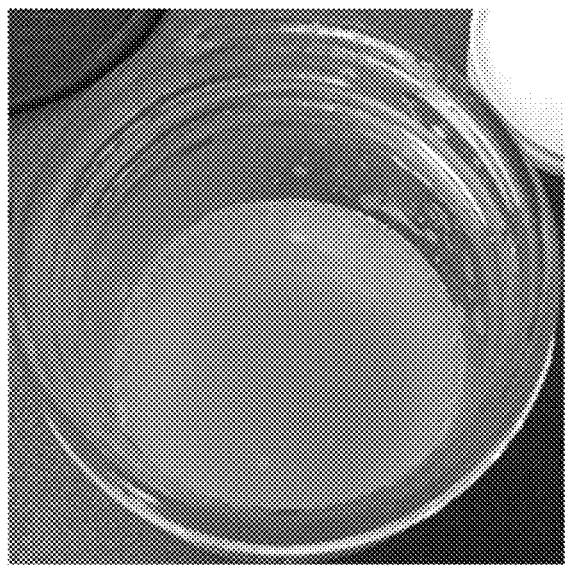
FIGS. 7 and 8 show results of vigorously mixing water, pomegranate seed oil, CBD, a vitamin blend, carbon dioxide, and xanthan gum as a carbohydrate stabilizer.
Figure 8:
Figure 9:
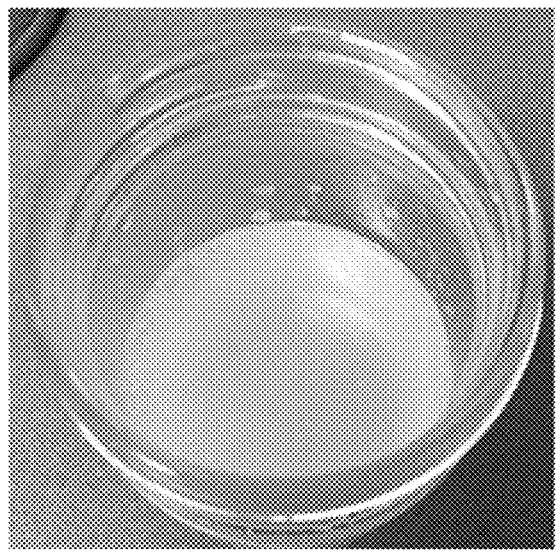
FIGS. 9 and 10 show results of vigorously mixing water, pomegranate seed oil, CBD, a vitamin blend, carbon dioxide, xanthan gum as a carbohydrate stabilizer, and alcohol in the form of an alcohol-based flavoring.
Figure 10:

FIG. 7 shows the result of dissolving CDB within pomegranate seed oil, carbonating the solution, then adding the vitamins, and xanthan gum as a stabilizer. A minuscule oil layer is present, and no solids are identifiable. FIG. 8 shows a suspension clarity example: a considerably dense haze is seen, indicating a much greater concentration of droplets within the solution. Through the addition of a small amount of an alcohol-based flavoring, the miscibility effectiveness is increased in the resulting beverage solution. It is suspected that the alcohol in the alcohol-based flavorings cause residual immiscible substances that may otherwise form a thin layer on top of the solution to be incorporated. FIG. 9 shows the effect of adding carbonated water, pomegranate seed oil, and then CBD, followed by a vitamin blend and xanthan gum as a carbohydrate stabilizer. This solution was mixed, followed by the addition of alcohol-based flavorings to a concentration of 0.25% (v/v) by volume before being mixed again. The result was a fully incorporated, fully stable emulsion. No oil layer is visible on the surface. FIG. 10 shows a demonstrated final clarity of this suspension.

Distilled full spectrum hemp oil (FSHO) has the viscous consistency of cold honey. As such, it presents a number of additional concerns when it comes to the addition of this oil to a carbonated, water-based beverage.

Figure 11:
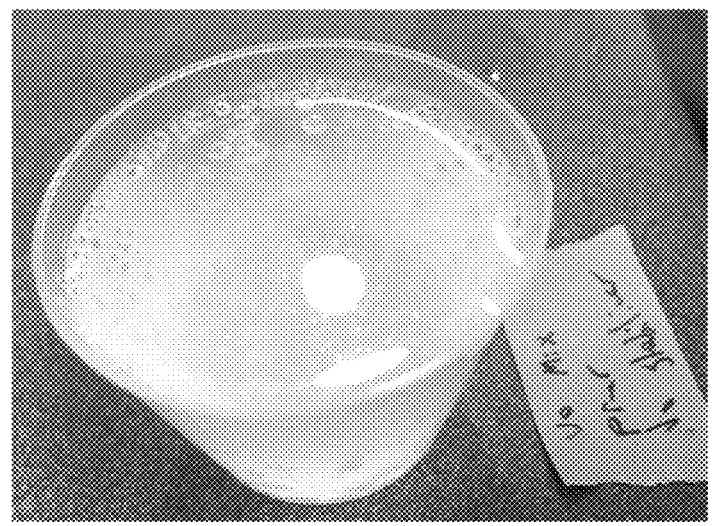
FIGS. 11 and 12 show the results of mixing water, pomegranate seed oil, distilled full spectrum hemp oil, carbon dioxide, and alcohol in the form of an alcohol-based flavoring without stabilizer.
Figure 12:
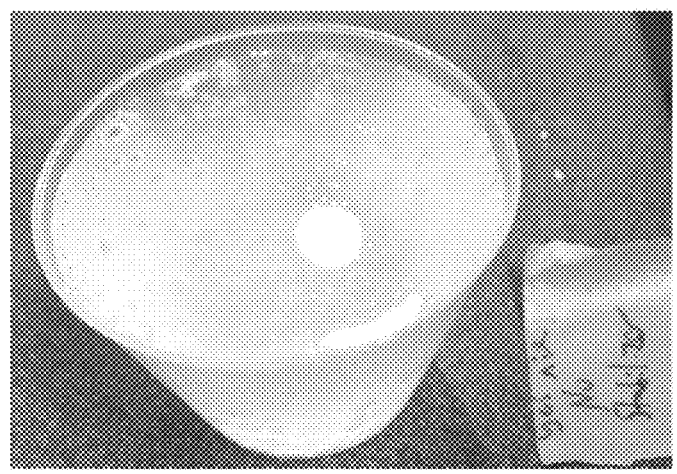
Figure 13:
FIG. 13 shows the result of mixing the same components as in FIGS. 11 and 12 but further including xanthan gum as a carbohydrate stabilizer. The pomegranate seed oil and the full spectrum hemp oil were pre-mixed before adding to the water. Oil droplets were still visible.

FIG. 11 shows a beverage sample made by mixing pomegranate seed oil, FSHO, vitamins, and alcohol-based flavorings one at a time with water, then shaking vigorously to combine and carbonating. A distinct oil layer results that is visible on the surface, with a multitude of denser oil droplets sitting on top of the carbonated solution and clinging to the sides of the container. The oil density within the body of the beverage increases when compared to the CBD isolate experiments. FIG. 12 shows a beverage sample made with the same components, only this time the FSHO was dissolved in pomegranate seed oil prior to adding the other ingredients. The result is a product that had a visible oil layer of uniform density on the surface, with greater oil dispersion density when compared to the CBD isolate trials. Due to its success in the CBD isolate trials, xanthan gum was again selected as a carbohydrate stabilizer to decrease the oily layer. At the original CBD isolate concentration, the xanthan gum additions did not perform well. The concentration of xanthan gum was pushed to the upper limits of acceptability in terms of mouth feel but still did not provide the level of complete or incomplete emulsion necessary. FIG. 13 a distinct oil layer resting on the surface of the xanthan gum trials, even at the highest concentration of stabilizer used (and still be considered a "beverage"). As assessed by the increased clarity of the solution and the bubbles forced to the edges of the container, the xanthan gum was likely binding with the water molecules and forcing the oil and gasses to the outside edges, effectively resulting in the opposite of the intended effect.

Because of the inability of xanthan gum to emulsify the pomegranate seed oil and FHSO mixture, liquid sunflower lecithin was tested as a possible emulsifying ingredient. Lecithin is comprised, in part, of the phospholipid phosphatidyl choline.

Figure 14:
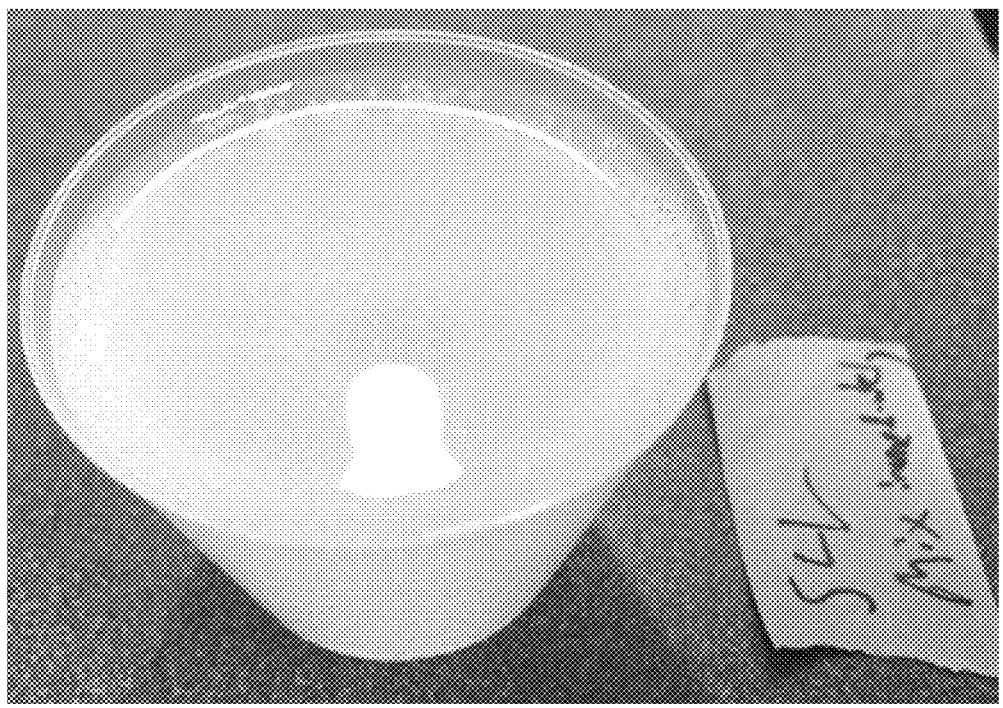
FIGS. 14 and 15 show the result of mixing the same components as in FIG. 13 except that lecithin was used as a stabilizer rather than xanthan gum.
Figure 15:
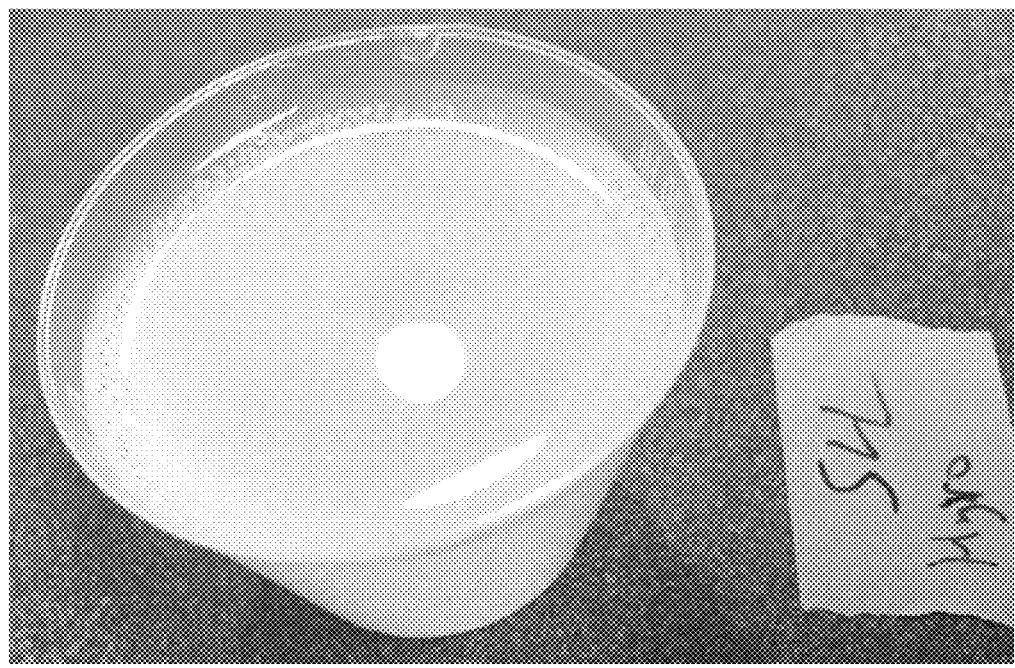
Figure 16:
FIG. 16 shows a side-by-side comparison of a number of methods of preparing a beverage containing water, pomegranate seed oil, distilled full spectrum hemp oil, carbon dioxide, and alcohol in the form of an alcohol-based flavoring. Left: No pre-mixing of pomegranate seed oil and full spectrum hemp oil and no stabilizer. Second-from-left: Pre-mixing of pomegranate seed oil and full spectrum hemp oil but no stabilizer. Middle: Pre-mixing of pomegranate seed oil and full spectrum hemp oil and use of xanthan gum as a carbohydrate stabilizer. Second-from-right: Pre-mixing of pomegranate seed oil and full spectrum hemp oil and use of non-hydrated lecithin as a stabilizer. Right: Pre-mixing of pomegranate seed oil and full spectrum hemp oil and use of hydrated lecithin as a stabilizer.

FIG. 14 shows a beverage sample using liquid sunflower lecithin as an emulsifier at 0.007% v/v. A dramatic increase in cloudiness and homogeneity is visible, with very few, very small oil droplets resting on the surface. Increasing the amount of lecithin used to 0.10% v/v did not have an apparent affect the amount of oil droplets remaining on the surface. Additionally, sunflower lecithin increased its effectiveness for oil-in-water emulsions if the phospholipids were exposed to water for a short period of time prior to blending. This "hydrating" process allowed the sunflower lecithin to expand and dissolve more readily in water. FIG. 15 shows a sample of 0.007% v/v liquid sunflower lecithin that had been hydrated and mixed into the beverage water base prior to having the CBD/pomegranate seed oils and vitamins mixed into it, resulting in a more complete and homogenous mixture than the lecithin without hydration. FIG. 16 shows a side-by-side comparison of all five pomegranate seed oil/FSHO trials. In addition to the overall opacity changes, it is worth noting the amount of oily residue that clings to the air-exposed portion of the sample jars without lecithin after mixing.

The pomegranate seed oil used in the present examples (Jedwards International, Inc., Braintree, Mass.) was a natural, cold-pressed and filtered triglyceride oil. The oil was an amber to dark orange colored liquid with a characteristic odor. The fatty acid profile of the pomegranate seed oil included 87.76% w/w C18:3 conjugates including punicic acid, 6.25% w/w C18:2 linoleic acid, 5.13% w/w C18:1 oleic acid, 3.03% w/w C16:0 palmitic acid, and 2.07% w/w C18:0 stearic acid.

The full spectrum hemp oil used in the present examples (Gold Oil Blend, FP-18-0487, CV Sciences, Las Vegas, Nev.) had a total cannabinoid content of 29.36% w/w, and a potential total cannabidiol compounds content of 25.4% w/w. The cannabinoids profile of the full spectrum hemp oil was 24.68% w/w cannabidiol, 0.75% w/w cannabidivarin, 0.67% w/w cannabidiolic acid, 0.36% w/w cannabigerol, 0.00% w/w cannabigerolic acid, 1.18% w/w cannabichromene, 0.14% w/w cannabinol, 0.61% w/w delta-9-tetrahydrocannabinol, and 0.97% w/w tetrahydrocannabinolic acid.

The lecithin used in the present examples (Sunflower Lecithin WD, product # SUN LEC WD, IFC Solutions, Linden, N.J.) was a viscous, dark brown, water-dispersible blend sunflower lecithin (greater or equal to 64% w/w) and non-lecithin emulsifiers (polysorbate, propylene glycol, distilled acetylated monoglycerides).

The vitamin mix used in the present examples (Product No. AF31825, Allen Flavors, South Plainfield, N.J.) was a mixture of vitamins B6, B12, C, D3, and E.

A number compositions were generated using the components and methods outlined above. The following concentrated syrups were each made into a total volume of 166.67 gal.

Syrup 1.

| Ingredients | Vendor | Product Code | lbs/166.67 gal |
| --- | --- | --- | --- |
| Water | | | 1318.58 |
| Sunflower Lecithin WD | IFC Solutions | SUN LEC WD | 1.25 |
| Pomegranate Seed Oil | Jedwards | S1450 | 1.25 |
| Full Spectrum Hemp Oil | CV Sciences | FP-18-0487 | 0.305 |
| Vitamin Premix | Allen Flavors | AF31825 | 5 |
| Alcohol-Based Flavorings | | | 68.55 |
| Citric Acid | | | 4.18 |

Pounds in 166.67 gal: 1408.53
Brix (finished syrup): 3.40 +/− 0.5
Density: 8.451 lbs/gal
Specific gravity: 1.01331
pH: 3.50 +/− 0.3

Syrup 2.

| Ingredients | Vendor | Product Code | lbs/166.67 gal |
| --- | --- | --- | --- |
| Water | | | 1328.7 |
| Sunflower Lecithin WD | IFC Solutions | SUN LEC WD | 1.25 |
| Pomegranate Seed Oil | Jedwards | 51450 | 1.25 |
| Full Spectrum Hemp Oil | CV Sciences | FP-18-0487 | 0.305 |
| Vitamin Premix | Allen Flavors | AF31825 | 5 |
| Alcohol-Based Flavorings | | | 58.17 |
| Citric Acid | | | 4.18 |

Pounds in 166.67 gal: 1406.33
Brix (finished syrup): 3.0 +/− 0.5
Density: 8.438 lbs/gal
Specific gravity: 1.01173
pH: 3.48 +/− 0.3

Syrup 3.

| Ingredients | Vendor | Product Code | lbs/166.67 gal |
| --- | --- | --- | --- |
| Water | | | 1356.69 |
| Sunflower Lecithin WD | IFC Solutions | SUN LEC WD | 1.25 |
| Pomegranate Seed Oil | Jedwards | 51450 | 1.25 |
| Full Spectrum Hemp Oil | CV Sciences | FP-18-0487 | 0.305 |
| Vitamin Premix | Allen Flavors | AF31825 | 5 |
| Alcohol-Based Flavorings | | | 31.67 |
| Citric Acid | | | 1.5 |

Pounds in 166.67 gal: 1401.41
Brix (finished syrup): 2.1 +/− 0.5
Density: 8.408 lbs/gal
Specific gravity: 1.00819
pH: 3.87 +/− 0.3

Syrup 1, Syrup 2, and Syrup 3 were made by mixing the lecithin and water and incubating the mixture for several minutes, mixing the pomegranate seed oil and the full spectrum hemp oil, mixing the lecithin/water mixture with the pomegranate seed oil and the full spectrum hemp oil, and then sequentially adding and mixing the remaining ingredients in the order listed.

Composition 1, Composition 2, and Composition 3 were then generated from Syrup 1, Syrup 2, and Syrup 3, respectively, by diluting 1 part of each syrup with 5 parts water to a final volume of 1,000 gallons, carbonating to 1.8-2.0 volumes of $CO_2$, sealing in containers, and tunnel pasteurizing.

The resulting compositions were stable suspensions with little to no unsuspended residual oil. Compositions 1, 2, and 3 each had a titratable acidity of 0.05 w/w. IN VITRO ASSESSMENT OF SYNERGISTIC EFFECTS OF FULL

SPECTRUM HEMP OIL, POMEGRANATE SEED OIL AND LECITHIN ON CD4+ T-CELLS

This study characterizes the immuno-modulatory effect of cannabidiol (CBD) and full spectrum hemp oil (FSHO) in CD4+ T cells and assesses the potential synergistic interaction among FSHO, punicic acid, and lecithin in this regard. This study also assesses the potential effects of CBD in glucose metabolism in activated T-cells and explores correlations with the activation and function of these immune cells.

Spleens from wild-type (WT) mice were collected and a single-cell suspension obtained. CD4+ T cells were sorted and plated in pre-coated 96-well plates with α-CD3 and α-CD28 T-cell markers. These cells then were treated with several doses of FSHO alone or in the presence of increasing concentrations of lecithin and/or pomegranate seed oil. FSHO, comprised of approximately 25% (v/v) cannabidiol (CBD) was obtained from the cold-pressed seeds of the *Cannabis sativa* plant. Cells were stimulated with PMA and ionomycin followed by a forty-eight-hour post-treatment pro-inflammatory cytokine profile assessed by a cytokine bead array.

Figure 17A:
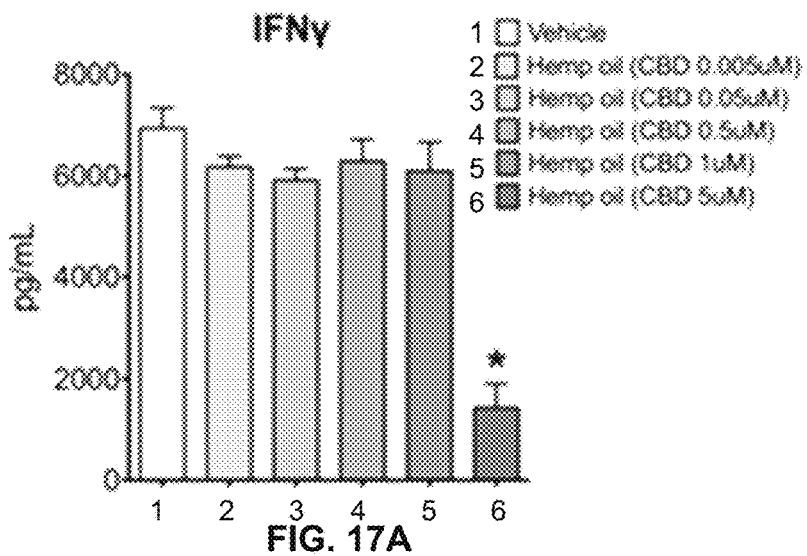
FIGS. 17A-F show the production of inflammatory cytokines IFNγ (FIGS. 17A-17C) and IL-17 (FIGS. 17D-17F) by CD4+ T cells treated with full spectrum hemp oil only (FIGS. 17A and 17D), full spectrum hemp oil and pomegranate seed oil (FIGS. 17B and 17E), or full spectrum hemp oil, pomegranate seed oil, and lecithin (FIGS. 17C and 17F). *p<0.05.
Figure 17B:
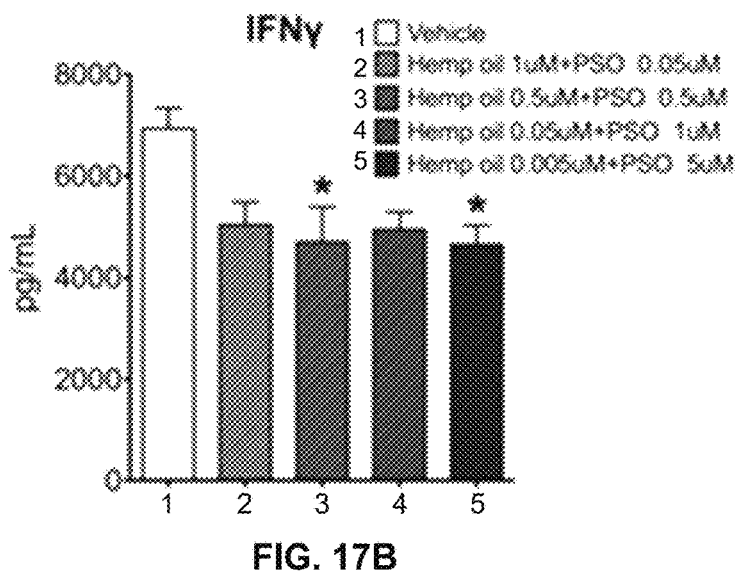
Figure 17C:
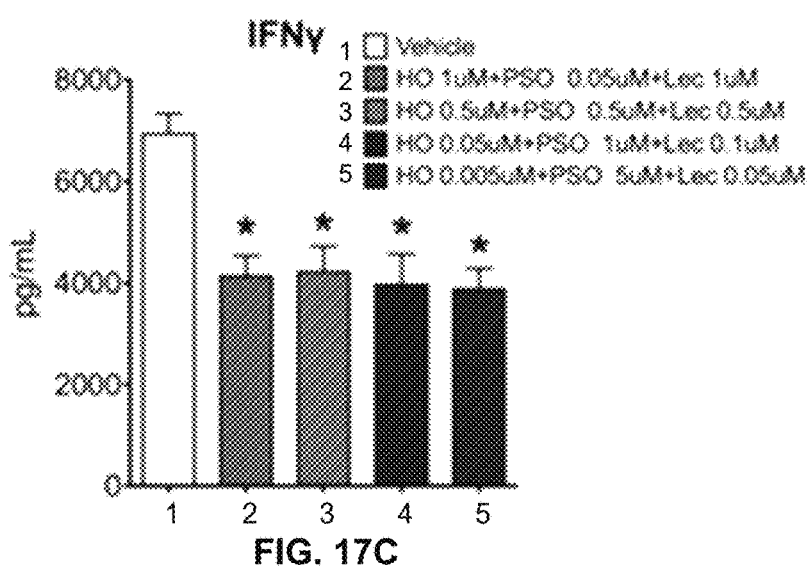
Figure 17D:
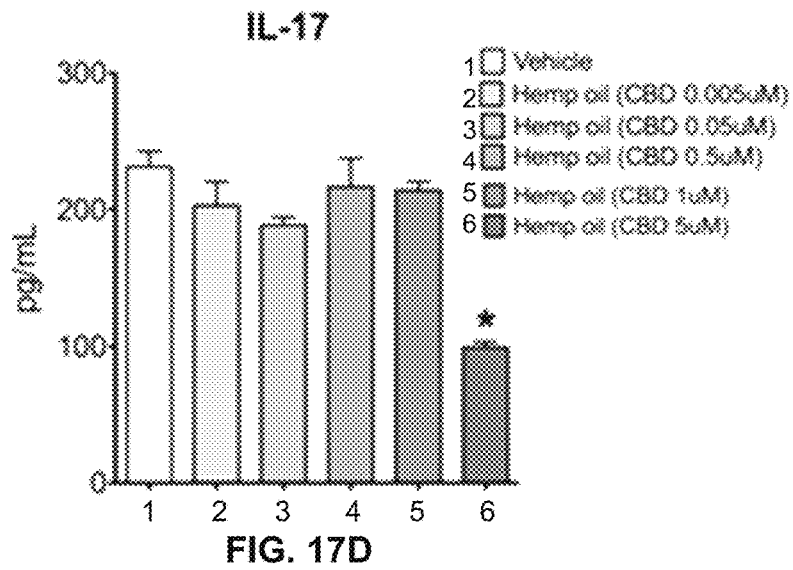
Figure 17E:
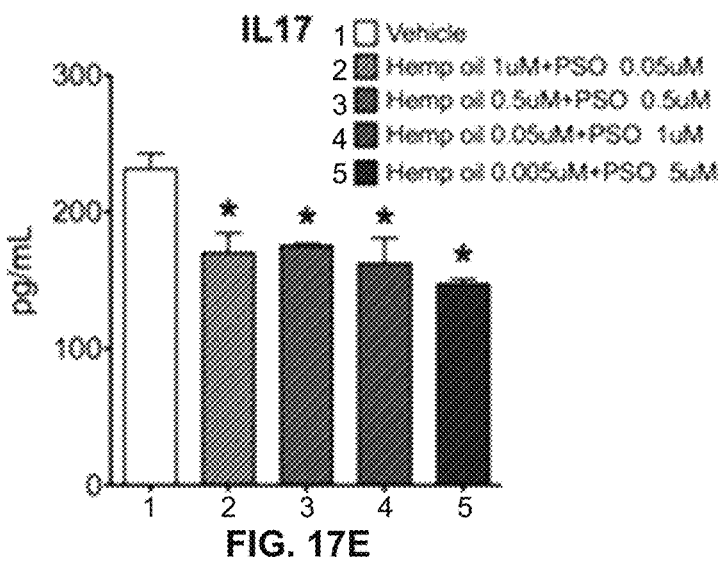
Figure 17F:
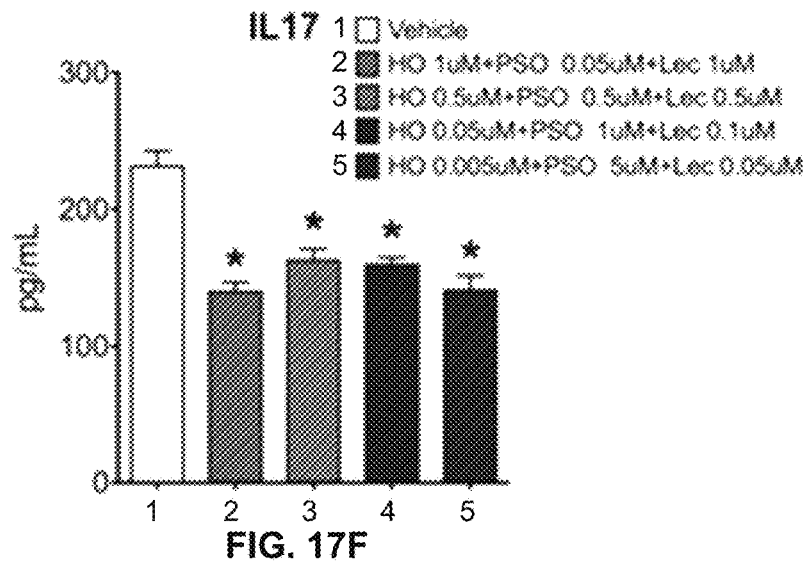
Figure 18:
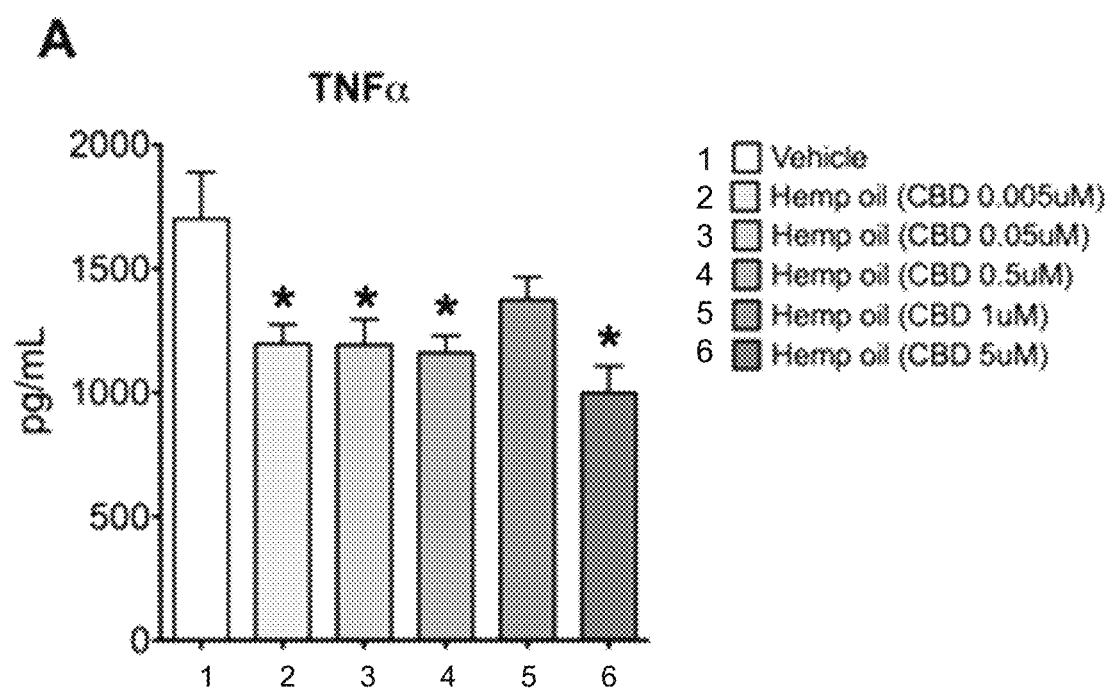
FIG. 18 shows the production of TNFα by CD4+ T cells treated with full spectrum hemp oil. *p<0.05.

FSHO treatment at a CBD dose of 5 micromolar (μM) significantly reduced pro-inflammatory cytokine production in WT CD4+ T cells, while administration of low doses of FSHO did not produce an apparent effect on IFNγ or IL-17 levels (see FIGS. 17A and 17D). Addition of pomegranate seed oil drastically increased the anti-inflammatory effect of FSHO, leading to a significant inhibition of both IL-17 and IFNγ production at lower doses of FSHO treatment (see FIGS. 17B and 17E). FSHO administration together with pomegranate seed oil and lecithin led to a more accentuated decrease of both pro-inflammatory cytokines reported at all tested doses (see FIGS. 17C and 17F). CD4+ T cell TNFα production was significantly decreased by FSHO treatment. In contrast to the FSHO effect reported in IL-17 and IFNγ secretion, low doses of FSHO significantly suppressed TNFα expression in vitro (see FIG. 18).

The significant decrease of pro-inflammatory cytokine production reported at low and high doses of FSHO led to the exploration of FSHO effects on CD4+ T-cell proliferation and metabolism of T-cells. In order to assess proliferation, CD4+ T-cells from WT mice were sorted and labelled with carboxyfluorescein succinimidyl ester (CFSE). Activated T-cells presented high proliferative rates as a response to external threat or input. FSHO administration of CBD at 5 μM significantly reduced the proliferative index of CD4+ T-cells compared to the untreated group (see FIG. 19A).

Figure 20A:
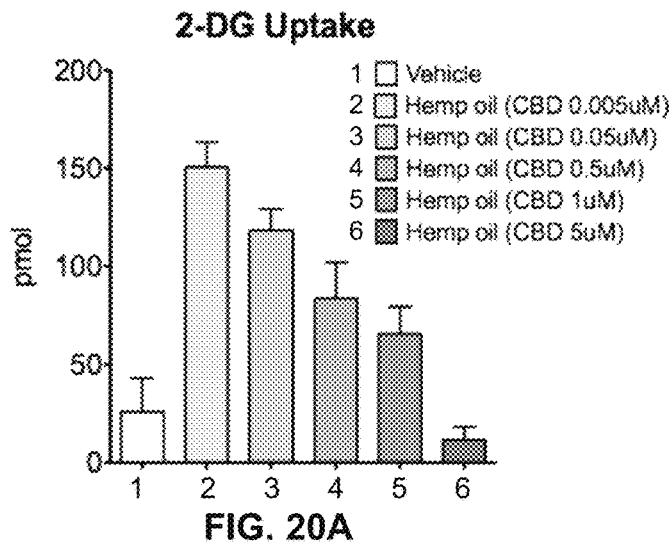
FIGS. 20A-C show glucose uptake as measured by 2-deoxyglucose uptake by CD4+ T cells treated with full spectrum hemp oil only (FIG. 20A), full spectrum hemp oil and pomegranate seed oil (FIG. 20B), or full spectrum hemp oil, pomegranate seed oil, and lecithin (FIG. 20C).
Figure 20B:
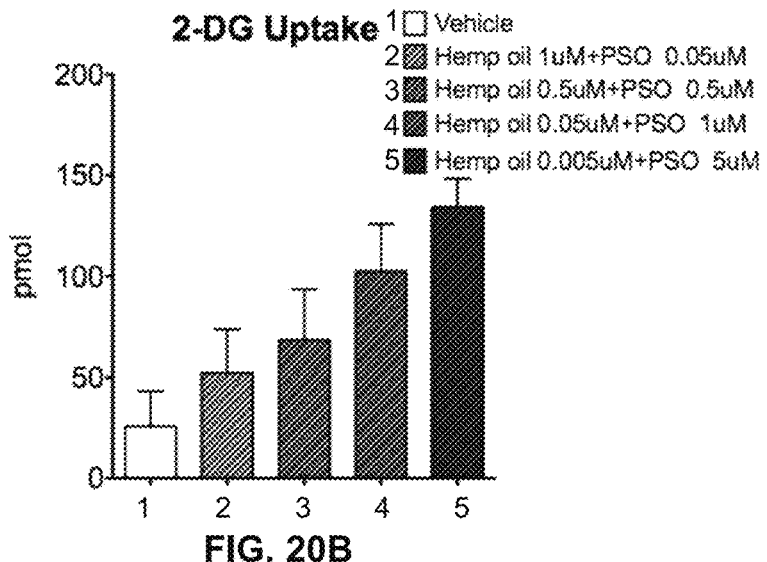
Figure 20C:
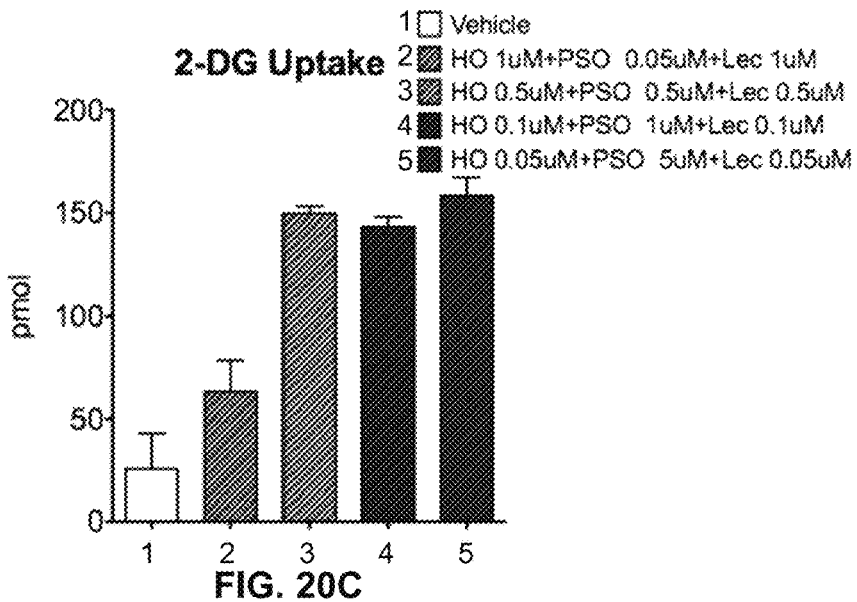

Upon the initiation of the immune response, CD4+ T-cells undergo a significant metabolic switch characterized by higher glucose uptake and lactate production to quickly produce high levels of energy and successfully execute their functions. Lactate dehydrogenase (LDH) is the enzyme responsible of the last step of the glycolysis that consists in the generation of lactate. FSHO administration of CBD at a 5 μM dose significantly suppressed LDH activity, leading to lower levels of lactate and an overall decrease of the glycolytic rate (see FIG. 19B). Moreover, FSHO decreased glucose uptake by CD4+ T-cells (see FIG. 20A), but the addition of pomegranate seed oil and lecithin provided an increased ability to take up glucose by CD4+ T-cells (see FIGS. 20B and 20C).

These results indicated that FSHO by itself can suppress pro-inflammatory cytokine production in T-cells but that high doses of FSHO are required to reduce the expression of certain pro-inflammatory cytokines, such as IL-17 and IFNγ. However, the addition of pomegranate seed oil and lecithin to FSHO significantly reduces the concentration of FSHO required for the reduction of inflammatory cytokine expression. Moreover, treatment of T-cells individually with pomegranate seed oil, lecithin or FSHO indicates a lower suppression effect on pro-inflammatory cytokine production than when used in combination. FSHO administration together with pomegranate seed oil and lecithin significantly accentuated FSHO impact on the pro-inflammatory cytokine profile, demonstrating a potential interaction between FSHO with pomegranate seed oil and lecithin that increases FSHO anti-inflammatory effects in CD4+ T-cell. In addition, FSHO administration reduced both proliferative index and glucose metabolism in CD4+ T-cells. While FSHO alone suppressed glucose uptake by CD4+ T-cells, the addition of FSHO in combination with pomegranate seed oil and lecithin rescued this phenotype and caused a dose-dependent increase in glucose uptake.

In addition to the impact to the cytokine profile, FSHO influenced the overall activation of CD4+ T-cells, possibly by regulating immune-metabolic mechanisms, and exhibited an overall synergistic anti-inflammatory effect when used in combination with pomegranate seed oil and lecithin.

What is claimed is:

1. An emulsion consisting essentially of water, pomegranate seed oil, dissolved carbon dioxide, lecithin, and hemp oil, wherein the hemp oil and the pomegranate seed oil are stably suspended within the water.

2. The emulsion of claim 1, wherein:
   the water is present in the emulsion in an amount of at least 95% w/v;
   the lecithin is present in the emulsion in an amount from 0.001% w/v to 0.1% w/v;
   the pomegranate seed oil is present in the emulsion in an amount from 0.001% w/v to 0.1% w/v;
   the pomegranate seed oil is at least 25% w/w punicic acid;
   the hemp oil is present in the emulsion in an amount from 0.0005% w/v to 0.05% w/v; and
   the hemp oil is at least 10% w/w cannabinoid.

3. The emulsion of claim 1, wherein the emulsion has no more than 0.01% w/v of a combined total of xanthan gum, polysorbate, propylene glycol, and distilled acetylated monoglycerides.

4. The emulsion of claim 1, further consisting essentially of from 0.05% w/v to 5% w/v alcohol.

5. The emulsion of claim 1, further consisting essentially of from 0.05% w/v to 5% w/v citric acid.

6. The emulsion of claim 1, wherein the hemp oil is full spectrum hemp oil.

7. The emulsion of claim 1, further consisting essentially of a vitamin selected from the group consisting of vitamin A, vitamin B1, vitamin B2, vitamin B3, vitamin B5, vitamin B6, vitamin B9, vitamin B12, vitamin C, vitamin D3, vitamin E, vitamin K1, vitamin K2, vitamin H, and combinations thereof.

8. The emulsion of claim 1, further consisting essentially of a mineral selected from the group consisting of boron, calcium, chloride, chromium, cobalt, copper, fluorine, iodine, iron, magnesium, manganese, molybdenum, nickel, phosphorous, potassium, selenium, silicon, sodium, strontium, sulfur, vanadium, zinc, and combinations thereof.

9. The emulsion of claim 1, further consisting essentially of abscisic acid.

10. The emulsion of claim 1, further consisting essentially of a component selected from the group consisting of alpha galactosidase, amylase, bromelain, cellulase, papain, peptidase, protease, proteolytic enzymes, superoxide dismutase, trypsin, betaine, casein, glutamic acid, L-alanine, L-arginine, L-cysteine, L-glutamine, L-glycine, L-histidine, L-isoleucine, L-leucine, L-lysine, L-methionine, L-ornithine, L-phenylalanine, L-proline, L-taurine, L-threonine, L-tryptophan, L-tyrosine, L-valine, N-acetyl-L-cysteine, protein soluble soy, soy protein isolate, whey protein isolate, and combinations thereof.

11. The emulsion of claim 1, further consisting essentially of an antioxidant selected from the group consisting of neoflavonals, tocopherol, tocotrienol, lipoic acid, melatonin, superoxide dismutase, coenzyme Q10, alpha lipoic acid, vitamin A, chromium biotin, selenium, ascorbic acid, and combinations thereof.

12. The emulsion of claim 1, further consisting essentially of a carotenoid selected from the group consisting of α-carotene, β-carotene, γ-carotene, δ-carotene, ε-carotene, lycopene, cryptoxanthin, zeaxathin, apocarotenal, astaxanthin, canthaxanthin, lutein, lutein esters, and combinations thereof.

13. The emulsion of claim 1, further consisting essentially of a flavonoid selected from the group consisting of esveratrol, quercetin, rutin, catechin, epicatechin, epigallocatechin, epigallocatechin gallate, proanthocyanidin, and combinations thereof.

14. The emulsion of claim 1, further consisting essentially of an isoflavone selected from the group consisting of genistein, daidzein, biochanin A, formononetin, and combinations thereof.

\* \* \* \* \*